United States Patent [19]
Lutz et al.

[11] Patent Number: 5,750,139
[45] Date of Patent: May 12, 1998

[54] TRANSDERMAL THERAPEUTIC SYSTEM FOR THE DELIVERY OF 5,6-BENZO-ALPHA-PYRONE

[75] Inventors: Jürg Lutz, Binningen; Henning F. Cierpka, Reinach, both of Switzerland

[73] Assignee: Drossapharm AG, Basel, Switzerland

[21] Appl. No.: 785,044

[22] Filed: Jan. 17, 1997

Related U.S. Application Data

[63] Continuation of Ser. No. 389,387, Feb. 16, 1995, abandoned.

[30] Foreign Application Priority Data

Feb. 18, 1994 [CH] Switzerland ............... 00 495/94

[51] Int. Cl.$^6$ .................................................. A61F 13/02
[52] U.S. Cl. .................................. 424/448; 424/449
[58] Field of Search ............................. 424/448, 449

[56] References Cited

U.S. PATENT DOCUMENTS

| | | | |
|---|---|---|---|
| 5,066,494 | 11/1991 | Becher | 424/448 |
| 5,424,320 | 6/1995 | Fortin | 514/337 |
| 5,505,956 | 4/1996 | Kim | 424/448 |
| 5,525,626 | 6/1996 | Thornes | 514/457 |

*Primary Examiner*—D. Gabrielle Phelan
*Attorney, Agent, or Firm*—Anderson, Kill & Olick, P.C.

[57] ABSTRACT

Sufficiently high blood benzopyrone levels cannot be achieved on oral administration of benzopyrone. From the point of view of pharmacokinetics and chronic application, the use of benzopyrone as an ointment is not optimal because the blood levels thus achievable cannot be controlled. It has now surprisingly been found that benzopyrone in a particular formulation as part of a transdermal dermal therapeutic system (TDS), after application to the skin, is released to the skin in a constant manner as a function of time and over a longer period owing to the absorption of perspiration, and that constant therapeutically effective blood and tissue levels of benzopyrone are achieved in humans, which levels are a factor of 50 higher than those following the oral administration of the same doses of benzopyrone.

4 Claims, No Drawings

TRANSDERMAL THERAPEUTIC SYSTEM FOR THE DELIVERY OF 5,6-BENZO-ALPHA-PYRONE

This is a continuation of application Ser. No. 08/389,387 filed Feb. 16, 1995, now abandoned.

BACKGROUND OF THE INVENTION

1. Field of the Invention

The invention relates to a transdermal therapeutic system containing at least one neutral or carboxylic acid-based active ingredient wherein the active ingredient:

a) less than 1% in water, b) greater than 10% in 70% ethanol, c) greater than 35% in chloroform and d) greater than 60% in pyridine.

The active ingredients belong to the following groups consisting of:

A) Neutral active ingredients
   a) Lower alkyl, hydroxy-lower alkyl, hydroxy-lower alkoxy-lower alkyl and benzyl esters of a carboxylic acid-based active ingredient as defined under B;
   b) Essential oils;
   c) Neutral substances having a benzopyrone skeleton;

B) Carboxylic acid-based active ingredients selected from the group consisting of the nonsteroidal antirheumatics, preferably those which are derived from acetic acid, from propionic acid or from a hydroxylated or acetoxylated benzoic acid, as well as carboxy-lower alkyl esters of such carboxylic acids.

Regarding Aa)

Lower alkyl, hydroxy-lower alkyl, hydroxy-lower alkoxy-lower alkyl and lower alkoxy-lower alkyl esters of a carboxylic acid-based active ingredient are those having not more than 4 carbon atoms in the ester radical, for example the corresponding methyl, ethyl, propyl or butyl esters and hydroxyethyl, hydroxyethoxyethyl, methoxyethyl and ethoxymethyl esters. Examples of such esters are methyl salicylate, ethyl salicylate, hydroxyethyl salicylate, ethyl p-hydroxybenzoate, hydroxyethyl 0-acetylsalicylate and the hydroxyethoxyethyl esters of flufenamic acid (etofenamate).

Regarding Ab)

Skin-tolerated essential oils, such as camphor oil, eucalyptus oil, lavender oil, pine needle oil, pine oil, pine kernel oil, rosemary oil, camomile oil, coriander oil, melissa oil or juniper oil, are mentioned as essential oils, but in particular components thereof, such as camphor, azulene, chamazulene, menthol, cineol, carvacrol, thymol or borneol, and their esters, such as bornyl acetate, bornyl chloride or bornyl salicylate.

Regarding Ac)

In particular, unsubstituted 5,6-benzo-alphapyrone (coumarin) as well as its derivatives hydrogenated in the pyrone ring, such as dihydro- or tetrahydrocoumarin, and coumarins having lower alkyl or lower alkoxy-lower alkyl groups in the 3, 4, 5, 6 or 8 position of the benzopyrone ring system and corresponding coumarins substituted in the 7 position by esterified or etherified hydroxyl.

In the above neutral substances having the benzopyrone skeleton, lower alkyl, lower alkoxy-lower alkyl, hydroxy-lower alkyl, lower alkoxy, hydroxy-lower alkoxy-lower alkyl, hydroxy-lower alkoxy-lower alkoxy and lower alkylcarbonyloxy have not more than 4 carbon atoms and denote, for example, methyl, ethyl, methoxyethyl, ethoxymethyl, hydroxyethyl, hydroxyethoxyethyl, hydroxyethoxyethoxy, acetyl or propionyl radicals, and halogen is preferably fluorine but also chlorine or bromine.

Among the neutral substances having the benzo-pyrone skeleton, the preferred active ingredient is 5,6-benzo-alpha-pyrone, abbreviated below to benzopyrone.

Regarding B)

Carboxylic acid-based active ingredients selected from the group consisting of the nonsteroidal antirheumatics are, for example, diclofenac, felbinac, flufenamic acid, ibuprofen, indomethacin, indoprofen, ketoprofen, tolmetin, salicylic acid, acetylsalicylic acid or p-hydroxybenzoic acid, as well as compounds of this group which are esterified with a carboxy-lower alkyl group, for example the carboxymethylester of indomethacin (acemetacin).

2. Description of the Prior Art

It is known that benzopyrone has antiphlogistic analgesic as well as antiedematous and lymphokinetic properties. Owing to these pharmacological properties, benzopyrone-containing drugs are used for the treatment of various, especially venous, vascular diseases and also for the treatment of protein-rich edemas, in particular for the therapy of protein-rich lymphedemas. The vascular diseases treatable with benzopyrone preparations include chronic venous insufficiency and phlebitis. In recent years, benzopyrone has also been used for the treatment of cancers.

In the case of many drugs, it is desirable to achieve uniform and long-lasting, therapeutically adequate blood levels. This can be achieved, for example, orally by means of a so-called slow-release formulation or transdermally by means of an ointment or the like. It is now known that benzopyrone can be applied percutaneously, in the form of an ointment or of a gel. This method of application via the skin has the advantage of substantially avoiding a "first pass" metabolism of the active ingredient in the liver. This percutaneous application of benzopyrone in the form of an ointment or of a cream, as disclosed, inter alia, also in U.S. Pat. No. 5,096,887, permits therapeutic use on relatively large skin areas in individual cases and for a short period. However, it is not possible to provide exact information about the particular absorbed dose in the case of such an application, particularly in view of the known, individually very different skin penetration (absorptivity) described in more detail below. Owing to the resulting possibility of an overdose and the associated potential adverse reactions, such percutaneous administration forms are, from the point of view of drug safety, unsuitable for continuous administration. However, it is precisely continuous administration which is essential for a successful treatment of chronic diseases of the above-mentioned type with benzopyrone.

A further disadvantage of the above-mentioned percutaneous preparations is that they liberate benzopyrone at an exponentially decreasing rate (1st or 2nd order pharmacokinetics). In order nevertheless to achieve more or less constant absorption of an active ingredient through the skin, the application must accordingly be repeated very frequently, which is troublesome for the patient and, owing to the frequently poor discipline of the patients, disadvantageous for the success of the therapy.

Little was known to date about the penetration of benzopyrone through the human skin.

The skin penetration of benzopyrone in the rat was described in the publication by Ritschel and Hussain (Meth. Find. Exptl. Clin. Pharmacol. 10, 165–169 (1988)). The authors applied 1 g of a 5% benzopyrone ointment to three different rats, over a skin area of 30 cm$^2$ in each case. From this publication (Table 3 therein), it is evident that a very large interindividual mean error of the skin permeabilities of benzopyrone occurred in the test series. Thus, the unabsorbed proportion of benzopyrone after 12 hours in the case of the three rats was 1.95 or 13.24 or 42.8 percent by weight, based on the originally applied benzopyrone dose. According to FIGS. 3 and 5 of this publication, individual absorption through the rat skin is nonlinear, i.e. does not exhibit 0 order kinetics ("there is a deviation from the zero-order absorption profile"; cited from page 167/168).

These results indicate that very different absorption rates are to be expected when benzopyrone is applied as an ointment, and that this administration form is unsuitable for long-term therapy simply for this reason.

In this context, however, it should be pointed out that even results which are more positive than the above-mentioned results of penetration tests in rats cannot be directly applied to humans: in the case of the above application of the ointment over 30 cm$^2$ of the rat skin, the ratio of application area to body weight is 120 cm$^2$/kg if the normal weight of a rat is assumed to be 250 g. Extrapolated to an adult weighing 75 kg, the corresponding application area (assuming the same penetration properties of the skin) would have to be 9000 cm$^2$, i.e. about 50% of the total skin surface. For this reason, too, direct comparisons of skin penetration between rats and humans are permissible only to a limited extent. Apart from this, the human skin is substantially more poorly penetrable than the skin of rats: for example, according to another publication by the same authors (Ritschel and Hussain, Arzneimittelforschg. 38, 1630–1632, 1988), rat skin permits the active ingredient griseofulvin to penetrate 14 times more readily than human skin used as a comparison, and the insecticide cypermethrin actually penetrates rat skin 20 times more readily than human skin (Scott and Ramsay, J. Invest. Dermatol. 89, 142–146, 1987).

Transcutaneously applicable active ingredients can be administered not only in the form of ointments, etc. but in principle also in the form of so-called transdermal therapeutic systems (TDS). A TDS is known to be a sticking plaster-like device having an active ingredient reservoir which contains the active ingredient in the form of a pharmaceutical formulation and releases it to the skin over a relatively long period.

Since the human skin has in principle very poor penetrability, in view of a person skilled in the art far from all active ingredients can be administered by means of a TDS, especially since its area and the amount of active ingredient applicable via this area onto and through the skin are very limited: according to EP-A-0 391 172 (page 3, line 34, therein), active ingredients are suitable for use in a TDS only if their daily dose is less than 50 mg.

Since, in oral administration, the benzopyrone dose therapeutically used and about 100% absorbed is 100–400 mg/day, and in published clinical studies up to 7 g orally per day have already been administered for experimental purposes, it did not appear very promising to adopt the approach involving the development of a transdermal therapeutic system, because these systems, as mentioned above, are in principle suitable only for the application of small to medium amounts of readily penetrating active ingredients, and because the application area cannot be made as large as desired.

In the case of the TDS usual today, which have matrix systems, the active ingredient is distributed in the form of islands (EP-A-0 391 172) or in another form in a water-insoluble polymer matrix. In these cases, however, only a very limited amount of active ingredient can in principle be taken up by this polymer matrix.

The above-mentioned statements clearly show why mainly oral preparations and only relatively very few transdermal therapeutic systems are available on the drug market for human therapeutic purposes.

SUMMARY OF THE INVENTION

It is the object of the invention to provide a drug for transdermal administration of at least one active ingredient having the physical properties defined in the preamble of claim 1, which drug does not have the disadvantages described above.

This object is achieved, according to the invention, by a drug having the characterizing features of claim 1, namely by virtue of the fact that the drug is in the form of a transdermal therapeutic system which contains the active ingredient or ingredients in a pharmaceutical formulation which can absorb perspiration and, owing to the influence of perspiration, permits a constant release of the active ingredient during at least 24 hours. Particularly advantageous embodiments of the invention and their use are described in the dependent claims. The formulation may be enclosed in a covering formed partly from a microporous membrane controlling the release of active ingredient.

The driving force for the migration of the active ingredient is the penetrating perspiration, which keeps the concentrated pharmaceutical formulation of the active ingredient, which is sparingly soluble in water and perspiration, at the edge of supersaturation. Uniform uptake of perspiration is controlled by the formulation itself, so that a membrane controlling the water absorption, as described in EP-A-0 391 172, is unnecessary.

The invention also relates to a process for achieving constant active ingredient levels, for example therapeutically effective benzopyrone levels in the blood and/or in the tissue, which comprises applying a transdermal therapeutic system (TDS) as claimed in any of claims 8 to 15 and containing an active ingredient defined in the claims, for example benzopyrone, to human skin. In particular, the drug is used for the treatment of lymphedemas, chronic venous diseases and chronic inflammations and of skin diseases or diseases close to the skin or for the treatment of skin cancer in the early or postoperative stage.

Another reason why the pharmaceutical industry has so far avoided development of a TDS suitable for human therapeutic purposes and designed to release benzopyrone is the assumption that benzopyrone is merely a prodrug, whereas its main metabolite, namely 7-hydroxybenzopyrone, is the actual active ingredient (cf. Sharifi et al., J. Irish Coll. Physicians Surgeons 22, 29–32, 1993).

Following an oral application, benzopyrone (I) undergoes a virtually quantitative "first pass" metabolism in the liver, i.e. it is metabolized immediately and virtually quantitatively in the liver. The benzopyrone (I) is irreversibly oxidized to 7-hydroxybenzopyrone (II), which immediately reacts further in an enzymatically coupled reaction to give the corresponding glucuronide (III) which is pharmacologically inactive. These reactions take place very rapidly, the second step of this coupled metabolic conversion taking place about 3.5 times faster than the preceding oxidation reaction, so that in practice only very small amounts of 7-hydroxybenzopyrone (II) and virtually no unchanged benzopyrone (I) enters the circulation from the liver. Accordingly, unchanged benzopyrone cannot reach the potential target tissue in the body following oral administration.

However, those skilled in the art assume that, outside the liver, a further equilibrium reaction takes place in which a part of the glucuronide (III) formed in the liver is hydrolyzed back to (II) before the rapid elimination in the kidney can occur. In other words, it is assumed that a certain amount of 7-hydroxypyrone is liberated again from the glucuronide (cf. Casley-Smith and Casley-Smith in: High Protein Oedemas and Benzopyrones, Chapter 9, page 423, Lippincott Co., Sydney, 1986).

For various reasons, those skilled in the art now regard 7-hydroxybenzopyrone as the actual effective agent. Sharifi et al., 1993 (cited above) give, for example on page 29 of the above-mentioned publication, the prior art as follows: "It is concluded that coumarin must be a prodrug and that the observed pharmacological effects result most likely from 7-hydroxycoumarin showing measurable concentrations in the systemic circulation."

Since according to current expert opinion 7-hydroxybenzopyrone is the actual active ingredient and hence as high blood levels as possible of 7-hydroxybenzopyrone (II) or (taking into account the above-mentioned hydrolytic equilibrium) of the corresponding glucuronide (III) are desirable, those skilled in the art believe that oral administration is superior to dermal application since the former leads to substantially higher blood concentrations of 7-hydroxybenzopyrone than the dermal administration forms.

That oral administration actually leads to substantially higher blood levels of 7-hydroxybenzopyrone than transdermal application is also confirmed by the clinical trials stated in Table 3 below.

The publication by Sharifi et al. (1993) discloses that the usually very small amount of II in addition to a large amount of III in the plasma (ratio 1:100) can be increased to 1:10 by very high oral doses of benzopyrone (for example 2 g orally). This finding which can be explained by acute saturation of the capacity of the glucuronization reaction in the liver has resulted, in more recent therapeutic studies, in the oral benzopyrone doses being further increased (up to 7 g/day) in the hope of also further increasing the blood level of the 7-hydroxybenzopyrone (II), which is regarded as the sole effective agent.

According to the publication by Sharifi et al. (1993), the blood levels of benzopyrone (I) however remain very low even in the case of very high oral doses of I, since the ability of the liver to oxidize benzopyrone, in contrast to glucuronization, is not limited by a lack of substrate even on administration of very high doses. The preference given to the oral administration of benzopyrone, which is usual in therapeutic practice, is accordingly based on the current opinion, considered to be true, that benzopyrone becomes effective only via the proven rapid and complete metabolism in the liver. It may be these last-mentioned reasons which, in spite of certain exploratory preliminary studies (cf. Ritschel and Barkhaus, Arzneimittelforschung 38, 1774–1777, 1988), have so far restrained the appropriately informed persons skilled in the art from the development of a benzopyrone-containing TDS which can be used for human therapeutic purposes, which is also technically very complicated, since this development must have appeared to them from the outset as being of little use compared with the oral administration form. This prejudice, which is understandable on the basis of the above statements, is expressed, for example, in the latest pharmacokinetic investigation, in which it is concluded that it is improbable that benzopyrone itself gives rise to significant pharmacological effects in the systemic circulation (Sharifi et al., 1993, page 32 therein): " . . . coumarin itself is unlikely to produce significant pharmacological effects in the system circulation."

There was therefore a very considerable prejudice against the development of a TDS containing benzopyrone, although such a possibility was in principle considered on the basis of the skin penetration in rats (Ritschel and Hussain, Meth. Find. Exptl. Clin. Pharmacol. 10, page 168, 1988, and Ritschel and Barkhaus, 1988, as cited above).

In general, all these studies are limited to investigations into matrix-controlled TDS, as is the attempt, described in German Patent 3,715,990 (Example 7), to polymerize a coumarin-containing mixture for the preparation of a matrix-controlled form of a transdermal system. However, the information in this German patent does not contain any details on the technical and human therapeutic realization of the invention. In particular, there is absolutely no indication as to whether the benzopyrone-containing polymer prepared from the polymerization mixture is at all capable of liberating benzopyrone, and whether and how any possible release takes place as a function of time, in particular whether it takes place uniformly. The stated patent contains no information regarding this minimum requirement essential for every novel TDS.

Accordingly, none of the above-mentioned articles and publications of the prior art suggest a method for the technical development of a benzopyrone-based TDS which can be used in practice, i.e. for human therapy, said development being known to be difficult.

From the fact that, in spite of the long-known observation that benzopyrone is capable of penetrating the skin, more specific information on the development of a TDS which can be used for human therapy has not appeared either in publications or in patents, it is to be concluded that the realization of such a project was not pursued for technical reasons or because of the prejudices described. The prior art known to date indicates that the partial object according to the invention, to develop a TDS which is based on the active ingredient benzopyrone and can be used for human therapy, has still not been achieved.

In overcoming the described prejudice that as high a blood level as possible of the 7-hydroxymetabolite of benzopyrone is desirable for achieving therapeutic effects since this metabolite is the active agent, it has now been surprisingly found that, when applied in the form of the TDS according to the invention, benzopyrone preferably accumulates in inflamed target tissues and displays its pharmacological actions there in concentrated form, and metabolic transformation of the benzopyrone highly concentrated in the target tissue, i.e. locally, into 7-hydroxybenzopyrone not being excluded as an action mechanism.

Moreover, this result of the transdermal application, according to the invention, of the benzopyrone as a TDS, in which the latter gives very high blood and tissue levels of unchanged benzopyrone while avoiding premature metabolism in the liver has a further considerable advantage:

Compared with the now generally conventional peroral administration, benzopyrone, when applied as a TDS (in spite of the relatively low absorbed dose), can accumulate in relatively high concentration in the target tissue without any unnecessary toxicological stress for the remainder of the body. The application, according to the invention, of benzopyrone as TDS is thus superior to the conventional oral therapy.

In the course of the development of a TDS which contains benzopyrone as active ingredient in a concentrated solution or microemulsion instead of in a polymer matrix, it was necessary to set the following special technical-physical requirements for the properties of the formulations to be used in the TDS to be developed or for the TDS as a whole:

The concentration of the benzopyrone in the pharmaceutical formulation must be as high as possible in order to ensure a sufficiently high concentration gradient for at least 24 hours when the TDS is used.

The dose released per unit time must be uniform and sufficiently high to fulfil the desired therapeutic purpose.

Perspiration from the skin, which always condenses under an occlusion, gives rise to a considerable problem. It was necessary to find a formulation which absorbs the continuously forming perspiration without undergoing an irreversible change, i.e. the solution or the microemulsion must not disintegrate when applied to the skin.

Under the usual storage conditions, the TDS must have a sufficiently long shelf life and must be heat-resistant. The difficulties of this stability requirement for a TDS were discussed in detail, for example, in EP-A-0 391 172.

The TDS must adhere to suitable skin areas for a sufficiently long time, sufficiently strongly and sufficently reliably.

Finally, the TDS must not have any adverse reactions giving rise to allergies or skin irritation.

The statements below now show that the above-mentioned very high requirements can be met by the drug according to the invention.

DETAILED DESCRIPTION OF THE PREFERRED EMBODIMENTS

For the technical-pharmaceutical development of a TDS with a benzopyrone-containing formulation, the release of the active ingredient from the benzopyrone containing formulation in the interior of the TDS onto the skin surface can be controlled in a manner known per se by means of a conventional microporous membrane. This microporous membrane consists, as a rule, of a material which is impermeable to the active ingredient and has a predetermined number of microscopic perforations of specified diameters. Such membranes are known to a person skilled in the art and are also commercially available. In addition to the dimensioning to be established and the properties of the membrane, the composition and stability of the formulation of the active ingredient in the interior of the TDS is of decisive importance for the suitability of such a TDS in practice. Suitable formulations are viscous solutions, gels, emulsions or microemulsions, which must have as high a concentration of active ingredient as possible in order to be able to keep the volume of the formulation in the active ingredient reservoir of the TDS as small as possible and at the same time to keep the amount of available active ingredient as large as possible. As already mentioned, the formulations must meet certain minimum requirements with regard to the shelf life, as well as with respect to separation with a change of the release kinetics on admission of perspiration.

Such a formulation for a TDS must be able to absorb up to 20% of water (as perspiration) which passes as a result of inverse osmosis through the skin into the formulation when the TDS is applied. If such a formulation were incapable of absorbing water, the microemulsion in the interior of the plaster would be broken or the solution or the gel would disintegrate, with the result that the characteristic of the active ingredient release would change and hence the TDS would cease to function. Suitable examples of TDS are described in Examples 1-9.

In the development of a TDS, it was necessary to solve the problem of maintaining the stability and function of the formulation, in spite of the penetration of considerable amounts of perspiration, which is to be expected especially with prolonged application.

The formulations selected were those which contained 5–50%, preferably 10–30%, of benzopyrone and, as base components, varying amounts of polymer compounds having an emulsifying action and optionally further formulation components, such as consistency factors, emulsifiers, solubilizers and solvents having penetration-enhancing properties. Such compounds are known from the prior art and are commercially available.

Suitable polymers having an emulsifying action are hydrophilic, hydrophobic and preferably water-soluble polymers having different chain lengths, preferably those selected from the group consisting of the polyalkylene glycols, for example corresponding polyethylene glycols.

Suitable consistency factors are, for example, higher fatty esters of polyols, for example of glycerol. Consistency factors contain, for example, corresponding mono- or diglycerides, for example of palmitic or stearic acid, or mixtures of such mono- or diglycerides, which are designated "glyceryl stearates" according to CTFA nomenclature. Cutina MD is mentioned as an example of a specific commercial product of this type.

Further suitable emulsifiers and/or solubilizers are anionic, cationic and preferably nonionic emulsifiers. Suitable nonionic emulsifiers are preferably higher fatty alcohols having 8–24, preferably 16–18, C atoms, such as cetyl alcohol and stearyl alcohol, or polyglycol esters of higher fatty acids.

Special solubilizers contain compounds having large hydrophobic and hydrophilic groups, for example polyethoxylated fatty acid glycerides or fatty acid polyalkylene glycol esters, such as, for example, castor oil fatty acids. Specific examples of such products are Cremophors, such as Cremophor RH 40.

Suitable solvents having penetration-enhancing properties are skin-tolerated penetration enhancers known from the prior art and of low toxicity, in particular low molecular weight, polar compounds or mixtures thereof, for example dimethyl sulfoxide (DMSO), dimethylformamide (DMF) and/or N-methylpyrrolidone.

Conventional skin-colored aluminum foils, for example coated on both sides with polyethylene, can be used for the backing of the TDS.

The membranes used for controlling the diffusion of the active ingredient are commercial microporous polymer membranes which are provided by the manufacturer with an adhesive layer (generally acrylate or silicone adhesive) and with a backing which can be peeled off after production of the TDS and before application to the skin. These membranes are produced from a material directly fusible with the backing, for example from polyethylene. Corresponding membranes of cellulose, cellulose acetate, cellulose nitrate, polyamide or polysulfone are also known. The following may be mentioned as examples of preferred control membranes:

Cotran MSP 101088 (MSXE 61), Cotran 61588 (MSXE 62) and Cotran 9711 (MSX 1137) from 3M Company, the permeability of which to air serves as a measure of the control properties. Control membranes suitable for use have, for example, an air permeability of 50 ml in 5–150, preferably 20–85, seconds, depending on the degree of control desired. The absolute amount of benzopyrone available on the skin surface depends not only on the type and pore size of the control membrane but in particular also on its active (effective) area in the TDS. This area may be up to 300 $cm^2$, preferably 1–100 $cm^2$. The layer thickness of the formulation in a TDS is 0.1–10.0 mm, preferably 0.1–3.5 mm. The chosen layer thickness depends in particular on the intended duration of application of a TDS.

The best formulations which are resistant to perspiration have proved to be those containing polyalkylene glycol, in particular polyethylene glycols, especially PEG 400, optionally as a mixture with higher molecular weight polyethylene glycols, such as PEG 1540 or PEG 4000. Cremophors, in particular Cremophor RH 40, optionally with the addition of further skin-tolerated emulsifiers, such as mono- and/or diglycerides of fatty acids or higher fatty alcohols having 8–24, preferably 16–18, C atoms, such as cetyl alcohol, and conventional penetration-enhancing solvents, such as dimethylformamide, dimethyl sulfoxide and/or N-methylpyrrolidone.

The various test formulations were tested in the water absorption test with regard to their stability to perspiration. For this purpose, 50 ml of water or simulated perspiration were added slowly from a burette, while stirring, to 100 ml of each formulation until the formulation or microemulsion exhibited an abrupt increase in the Tyndall scattering at 610 nm, indicating a transformation of the solution or the microemulsion, with separation, into a macromycelial structure.

The best formulations can absorb at least 20% of water or perspiration without the solutions or the micromycelial structures of the microemulsions separating or detectably changing.

10 ml of each of the formulations which were successful in these tests were alternately either heated to +70° C. or cooled to below 0° C. for 8 h during the the day and in between (during the night) kept for 16 h at room temperature, in a test in a closed tube for 14 days. The best formulations also passed such a stability test lasting several days without detectable changes. These were then used for the preparation of the TDS mentioned below, and these were subjected to additional in vitro diffusion and active ingredient release tests before they were tested in a clinical. study.

In Examples 1–9 below, selected embodiments of the TDS according to the invention are described. However, the formulations mentioned there do not constitute a definitive list of the possibilities according to the invention. The starting materials and materials used are described sufficiently and in detail in published patents and in published surveys, are known to a person skilled in the art and are readily obtainable, so that there is no need at this point to refer to these known principles of the prior art. A person skilled in the art also knows that individual components among the stated formulation components may be replaced without inventive activity by other functionally equivalent conventional formulation components without departing from the scope of the invention.

EXAMPLE 1

120 g of benzopyrone, 240 g of Cremophor RH 40 and 240 g of polyethylene glycol 400 are mixed at 65° C. and stirred for 30 min at room temperature, and one gram of each homogeneous, clear mixture is filled without bubbles into a prepared control film already welded on three sides with a skin-colored polyethylene film and provided with an adhesive layer and backing, and then sealed by welding.

EXAMPLE 2

150 g of benzopyrone, 400 g of Cremophor RH 40, 420 g of polyethylene glycol 400, 20 g of Cutina MD and 10 g of cetyl alcohol are mixed at 65° C. and stirred for 30 min, and 1.3 g of the mixture are filled as in Example 1.

EXAMPLE 3

20 g of benzopyrone and 80 g of polyethylene glycol 400 are mixed at 60° C., dissolved by stirring at this temperature and then cooled within one hour while stirring. The clear mixture can be filled as described under Example 1.

EXAMPLE 4

200 g of benzopyrone, 790 g of polyethylene glycol 400 and 10 g of Cremophor RH 40 are mixed at 65° C., dissolved by stirring for half an hour and filled as described in Example 1.

EXAMPLE 5

100 g of benzopyrone, 200 g of Cremophor RH 40, 130 g of polyethylene glycol 1540, 510 g of polyethylene glycol 400, 30 g of polyethylene glycol 4000, 10 g of cetyl alcohol and 20 g of Cutina MD are mixed at 60° C. and cooled to room temperature within one hour. The resulting emulsion is filled as stated in Example 1.

EXAMPLE 6

60 g of benzopyrone, 120 g of Cremophor RH 40, 190 g of polyethylene glycol 400, 12 g of polyethylene glycol 4000, 12 g of Cutina MD and 6 g of cetyl alcohol are mixed at 60° C. and cooled to room temperature in the course of one hour while stirring. The viscous mixture is filled as stated under Example 1.

EXAMPLE 7

40 g of benzopyrone, 100 g of polyethylene glycol 400, 40 g of dimethyl sulfoxide and 20 g of Cremophor RH 40 are mixed at room temperature and, after stirring for 30 min, the clear mixture is filled as stated in Example 1.

EXAMPLE 8

200 g of benzopyrone, 400 g of polyethylene glycol 400, 150 g of dimethyl sulfoxide and 150 g of N-methylpyrrolidone are mixed at room temperature and stirred for 30 min, and the clear mixture is filled as stated in Example 1.

EXAMPLE 9

150 g of benzopyrone, 300 g of Cutina MD and 550 g of polyethylene glycol 400 are mixed at 60° C. and cooled slowly, within one hour, while stirring. The resulting mixture is thixotropic.

After reheating, this mixture can be filled as stated in Example 1.

The TDS to be tested were preselected by means of in vitro measurements of the dialysis of benzopyrone from the TDS investigated. For this purpose, the TDS available was stuck on the side facing the skin, i.e. the membrane side, by means of the adhesive layer, in a dialysis apparatus and was dialyzed against an excess of a solution of polyethylene glycol 400 or against an albumin or saline solution for at least 24 h. For the measurement of the diffused amount of benzopyrone, the absorbance of the dialysis solution was investigated spectroscopically at 274 nm. The half-lives for a 50% and 95% diffusion yield (t/2 50% and t/2 95%, respectively) were calculated from the linear part of the dialysis curves. For example, three selected formulations gave the following half-lives (Table 1):

TABLE 1

| Formulation No. | Control membrane Type MSXE No. | Half-life t/2 (h) |
|---|---|---|
| 1 | 61 | 17 |
| 1 | 62 | 6 |
| (according to Example 5) | 61 | 60 |
| (according to Example 5) | 62 | 27 |
| (according to Example 6) | 61 | 55 |
| (according to Example 6) | 62 | 21 |

With the use of a cellulose membrane having a pore size of 20 kD and with the use of a constant active surface area of 2.5 cm$^2$, the dialyzable amount of benzopyrone from a 20% formulation increases with increasing layer thickness until the saturation limit of the control membrane is reached and then remains constant in spite of a further increase in the layer thickness (Table 2):

TABLE 2

| Layer thickness of the TDS formulation (mm) | Amount of benzopyrone diffusing within 8 h (mg) |
|---|---|
| 0.1 | 8 |
| 0.2 | 14 |
| 0.4 | 14 |

The pore size of the control membrane considerably influences the amount of benzopyrone available on the skin surface, but this amount does not increase linearly with the pore size. When the same formulation was used, for example, the diffusion rate increased only by a factor of 1.6 when the pore volume was increased from 20 kD to 100 kD. By increasing the viscosity of the formulation, the rate of dialysis of the benzopyrone is considerably reduced.

The dose of benzopyrone reaching the skin surface in the membrane-controlled TDS according to the invention can thus be influenced by varying the following parameters:

Base formulation (composition, concentration of benzopyrone, viscosity)

Layer thickness of the formulation in the TDS

Choice of the control membrane with particular attention to
  the active surface area and
  the pore size.

Surprisingly, it was found in these in vitro tests that the active ingredient diffusion through the membrane, which, owing to the decreasing concentration as a function of time in the interior of the reservoir, should follow first or second order kinetics, exhibits linear kinetics in vitro owing to the absorption capacity of the preferred formulations for water.

Thus, as a result of the penetration of water, an unexpectedly uniform active ingredient release (constant as a function of time) through the membrane is obtained instead of the nonlinear kinetics to be expected as a result of the decreasing concentration of the active ingredient in the reservoir, i.e. an active ingredient release decreasing as a function of time. This finding requires a steadily increasing relative active ingredient release from the active ingredient formulation in comparison with the residual amount of active ingredient remaining in the reservoir, said release being effected osmotically by the penetration of water (or perspiration). This surprising finding was also confirmed in the clinical study with healthy volunteers, as described below. As shown below in Table 4, it was surprisingly found that constant blood levels of benzopyrone could be achieved with an unexpectedly high bioavailability of the active ingredient of 70% during a 96 hours application of a plaster according to the invention.

There were no exact requirements for the pharmacokinetic testing of the TDS according to the invention in humans.

In particular, there were no validated, i.e. sufficiently selective, sensitive and accurate analytical methods to enable sufficiently accurate measurement of the concentrations of the potentially effective components (benzopyrone and 7-hyroxybenzopyrone) in the blood in vivo after oral and transdermal administration. An object to be achieved before the beginning of the tests was accordingly to develop such a suitable analytical method for exactly monitoring the transdermal bioavailability of the TDS according to the invention. In this respect, there were only inadequate starting points: the sensitivity limits of the methods known from the prior art (Sharifi et al., 1993, FIG. 2 therein; Egan and O'Kennedy, J. Irish Coll. Physicians Surgeons 22, 72, 1993) were, for example, 20–36 ng of benzopyrone/ml of blood plasma.

For the envisaged human pharmacokinetic measurements of the absorption of benzopyrone from a TDS, it was therefore necessary first to work out an improved analytical method in which the sensitivity for I and II was increased by a factor of about 50 in order also to be able to obtain even more reliable information in the expected limiting concentration range up to 1 ng of benzopyrone/ml or 0.1 ng of 7-hydroxybenzopyrone/ml.

This was achieved by working out a novel, highly sensitive analytical method.

For better comparability, some pharmacokinetic preliminary experiments were carried out on one and the same healthy male volunteer (i.e. intra-individually). For example, a TDS according to the invention, containing 200 mg of benzopyrone and having an active area of 12 cm$^2$, was tested.

For comparison, in a further test, a film-coated tablet containing 100 mg of benzopyrone was administered to the healthy volunteer orally every 12 h over a total period of 6 days, which corresponded to the same nominal dose as in the TDS (200 mg of benzopyrone/24 h). The following blood levels were found (Table 3):

TABLE 3

| Site of appli-cation | Benzopyrone dose and duration of appplication | Benzopyrone (I) | | 7-OH-Benzo-pyrone (II) | | Ratio |
|---|---|---|---|---|---|---|
| | | c max (ng/ml) | t max (h) | c max (ng/ml) | t max (h) | I/II |
| oral | 2 tabl./24 h (2 × 100 mg/24 h) (6 days) | 2.5 | 3 | 4.2 | 4 | 0.6 |
| upper arm, inside | 1 TDS/24 h (1 × 200 mg/24 h) | 25.0 | 8 | 0.47 | 8 | 53.2 |
| chest skin | 2 TDS/48 h | 24.2 | 3 | 0.24 | 4 | 100.8 |

TABLE 3-continued

| Site of application | Benzopyrone dose and duration of appplication | Benzopyrone (I) c max (ng/ml) | t max (h) | 7-OH-Benzo-pyrone (II) c max (ng/ml) | t max (h) | Ratio I/II |
|---|---|---|---|---|---|---|
| | (2 × 200 mg for 48 h) | 36.4 | 34 | 0.65 | 29 | 56.0 |

The constant release of benzopyrone from the TDS via the skin was 35 mg/24 h in this case.

The above results show that, in the intraindividual comparison, a fundamentally different ratio of the blood levels of benzopyrone (I) to 7-hydroxybenzopyrone (II) is found, depending on whether administration is oral or transdermal: Although the benzopyrone dose (35 mg/24 h) taken up via the TDS was only 17.5% of the oral daily dose (orally administered amount: 200 mg/24 h) in the present case, the blood levels of benzopyrone (I) following transdermal application were 10 times higher than after oral administration and, conversely, the blood levels of II on application of benzopyrone as a TDS were 6–10 times lower than after administration of the oral dose.

The experimentally found ratio of benzopyrone (I) to 7-hydroxybenzopyrone (II) in the blood is thus a factor of 100–200 greater when I is applied as a TDS than after its oral administration (Table 3). Such a fundamentally different ratio of the blood levels of I to II after application of benzopyrone as a TDS was unexpected.

Since the blood levels were measured after oral administration in the steady state (i.e. at saturation of the blood), and it is known that the primary bioavailability of oral forms of benzopyrone is virtually 100%, it is possible to make the following statement about the difference between the two application forms: based on the same dose of benzopyrone (I) absorbed per day, the maximum blood levels of (I) after application as a TDS are 57 times higher than after oral administration. Also based on the same absorbed dose, the maximum blood concentrations of II are approximately comparable. Since, as is already evident from the above Table 3, comparably high blood levels of I occur even on the second day of application with the TDS, the result for the TDS containing 200 mg of benzopyrone is a relatively high bioavailability of 35%/48 h.

This bioavailability, which is very high for a TDS, could be further increased to 70% in 96 h in an experiment in which a TDS was worn for 4 days. This is an extremely high bioavailability for a TDS, since, for thermodynamic reasons, it is known that a residual amount of the active ingredient must always remain in the TDS. This experiment also shows that the release of benzopyrone over 96 h (4 days) takes place in a constant manner. In another experiment, another type of TDS according to the invention was used to test whether the release of benzopyrone from the TDS is truly constant over the total test time of 96 h and how rapidly the blood levels of benzopyrone decline after removal of the TDS (Table 4):

TABLE 4

| Application time (h) | Blood level of benzopyrone (I) (ng/ml) |
|---|---|
| Application of a TDS (200 mg of benzopyrone) over 96 hours | |

TABLE 4-continued

| Application time (h) | Blood level of benzopyrone (I) (ng/ml) |
|---|---|
| 48 | 5.5 |
| 72 | 6.1 |
| 82 | 8.7 |
| 96 | 6.6 |
| (after removal of the TDS) | |
| 3 | 2.4 |
| 6 | 0.8 |

This result confirms that the blood benzopyrone levels remain uniformly high over 4 days and decrease very rapidly after removal of the TDS.

The results obtained in the preliminary experiment were confirmed by a GCP-complying pharmacokinetic study with 14 healthy volunteers (Table 5):

TABLE 5

| Application time (h) | Benzopyrone (I) c max (mean value) (ng/ml) | 7-OH-Benzopyrone (II) c max (mean value) (ng/ml) | I/II |
|---|---|---|---|
| Single application of a TDS containing 200 mg of benzopyrone to 14 healthy volunteers | | | |
| 3 | 23.4 | 0.40 | 58.5 |
| 24 | 27.3 | 0.48 | 56.9 |
| (after removal of the TDS) | | | |
| 4 | 4.96 | 0.13 | — |

This clinical study, too, showed, after use of a TDS, a constant blood concentration of benzopyrone from the third to the final (24th) hour of application.

As is evident from Table 5, the blood benzopyrone levels had already decreased to less than 20% of the blood levels at 4 hours after removal of the TDS. The blood levels of 7-hydroxybenzopyrone also decreased rapidly. The steady state, i.e. the definitive level of the then constant blood benzopyrone level, was established after only 3 h.

The high effective yield of 70% in 96 h and the linear active ingredient release found over the total application time of 96 h show that the problems associated with the absorption of the perspiration could also be solved. It was found that the perspiration is not only absorbed by the benzopyrone formulations described in the Examples but permits the constant release of benzopyrone during a period substantially exceeding 24 hours.

A further positive result of the investigations is the excellent toleration and the good adhesion of the TDS described in the Examples.

The shelf life of the TDS according to the invention is also good.

The problem of realizing a feasible TDS suitable for human therapeutic purposes was thus solved.

The results obtained when the TDS according to the invention were used were in no way foreseeable on the basis of the prior art described at the outset.

We claim:

1. A transdermal therapeutic system, comprising an impermeable top layer; a microporous membrane welded to the impermeable top layer so that the impermeable top layer and the microporous membrane form together an inner space; and a pharmaceutical formulation contained in the inner space, wherein the pharmaceutical formulation contains as an active ingredient 5 to 50% by weight of 5,6-benzo-alpha-pyrone and is capable of absorbing perspiration and, as a result of the effect of perspiration, permits a constant release of the active ingredient during at least 24 hours.

2. A transdermal therapeutic system as claimed in claim 1, wherein the pharmaceutical formulation contains 10 to 30% by weight of 5,6-benzo-alpha-pyrone, 1 to 50% by weight of a solubilizer which contains compounds having hydrophobic and hydrophilic groups, and 15 to 85% by weight of one or more polyalkylene glycols.

3. A transdermal therapeutic system as claimed in claim 1, wherein the pharmaceutical formulation contains 10 to 30% by weight of 5,6-benzo-alpha-pyrone and 20 to 90% by weight of one or more polyethylene glycols having a molecular weight of 300 to 5,000.

4. A transdermal therapeutic system as claimed in claim 1, wherein the pharmaceutical formulation furthermore contains at least one of the following additives:

- 1 to 50% by weight of a solubilizer, which contains compounds having hydrophobic and hydrophilic groups,
- 1 to 35% by weight of a consistency factor selected from the group consisting of the glycerol sterates,
- 1 to 5% by weight of a fatty alcohol having 16 to 18 carbon atoms, and
- 1 to 30% by weight of one or more solvents selected from the group consisting of dimethyl sulfoxide, dimethylformanide and N-methylpyrrolidone.

* * * * *